_US005631002A_

United States Patent [19]
Yagi et al.

[11] Patent Number: 5,631,002
[45] Date of Patent: May 20, 1997

[54] LINIMENT FOR MELANIN INHIBITORS

[75] Inventors: Eiichiro Yagi; Hisayuki Komasaki; Yuki Shibata; Masako Naganuma; Minoru Fukuda, all of Yokohama, Japan

[73] Assignee: Shiseido Co., Ltd., Tokyo, Japan

[21] Appl. No.: 496,614

[22] Filed: Jun. 29, 1995

[30] Foreign Application Priority Data

| | | | |
|---|---|---|---|
| Jun. 29, 1994 | [JP] | Japan | 6-168673 |
| Jun. 29, 1994 | [JP] | Japan | 6-168679 |
| Jun. 29, 1994 | [JP] | Japan | 6-168681 |
| Jun. 29, 1994 | [JP] | Japan | 6-168685 |
| Mar. 10, 1995 | [JP] | Japan | 7-078478 |

[51] Int. Cl.$^6$ ............ A61K 7/021; A61K 7/48
[52] U.S. Cl. ............ 424/62; 424/195.1; 424/401; 424/63
[58] Field of Search ............ 424/195.1, 401, 424/62; 514/828, 844, 846, 847, 969

[56] References Cited

U.S. PATENT DOCUMENTS

| | | | |
|---|---|---|---|
| 4,983,385 | 1/1991 | Hasegawa et al. | 424/78 |
| 5,262,153 | 11/1993 | Mishima et al. | 424/62 |

*Primary Examiner*—Thurman K. Page
*Assistant Examiner*—Sharon Howard
*Attorney, Agent, or Firm*—Townsend & Banta

[57] ABSTRACT

An endermic liniment is provided which contains one of more of Piri-Piri extract, Pinon Negro extract, Pinon Blanco extract, or Cola de caballo extract. The endermic liniment exhibits superior hypochromic effects and whitening effects on pigment deposition, chloasma, freckles, liver spots, etc. after sunburn and is superior in terms of safety.

10 Claims, No Drawings

LINIMENT FOR MELANIN INHIBITORS

FIELD OF THE INVENTION

The present invention relates to an endermic liniment which, by containing either a Cola de caballo extract, Piri-Piri extract, Pinon Negro extract or Pinon Blanco extract, suppresses production of melanin and is effective in the prevention and improvement in conditions including pigment deposition, chloasma, freckles and liver spots after sunburn.

BACKGROUND OF THE INVENTION

The mechanism of the development of chloasma and such on skin, although there are some unknown details, is generally believed to be the formation of melanin pigment due to hormonal abnormalities or ultraviolet light stimulation from sunlight followed by abnormal deposition of this pigment in the skin. This melanin pigment which causes the coloring of the skin is produced in melanin producing granules (melanosomes) in melanin cells (melanocytes) between the epidermis and the corium. Melanin thus produced is then diffused to neighboring cells by means of osmosis. The biochemical reactions in the melanocytes are speculated as described below.

That is, the production process of the melanin pigment is as follows: tyrosine, one of the essential amino acids, becomes dopaquinone through the action of an enzyme tyrosinase, and this is then changed to a red pigment, to a colorless pigment and finally to melanin, which is black, by enzymatic as well as non-enzymatic oxidation.

Therefore, in order to suppress the production of melanin, it is important to suppress the first stage of the reactions, i.e. the action of tyrosinase.

However, compounds which suppress tyrosinase action, except for hydroquinone, work very slowly and do not give sufficient improvement in pigment deposition in the skin. On the other hand, hydroquinone, although its effects are recognized, has the problem of sensitization and, therefore, its uses are generally limited. For the purpose of improving its safety, attempts have been made to alter it to a monoester of a higher fatty acid, an alkyl monoether and such (Japanese unexamined patent publication Tokkai Sho 58-154507). However, esters are decomposed by hydrolytic enzymes in the body and therefore are not necessarily safe. Sufficiently safe ethers have not been obtained yet either.

For the purpose of solving these problems, the inventors investigated a wide variety of substances for the melanin production suppression effect, and discovered that Pinon Negro (scientific name: *Jastropha curcas* L.) extract, Pinon Blanco extract, Cola de caballo extract (scientific name: *Equisetum giganteum*) extract, and Piri-Piri (scientific name: *Cyperas spacelatus* Rottb (*C. articulatus* L.)) extract, had the melanin production suppression and tyrosinase inhibition actions. There has been no report on the melanin production suppression actions of these substances or their application as whitening agents.

SUMMARY OF THE INVENTION

In the present invention an endermic liniment is provided which characteristically contains one or more of the following: Pinon Negro extract, Piti-Piti extract, Cola de caballo extract or Pinon Blanco extract. The endermic liniment of the present invention exhibits superior hypochromic effects and whitening effects on pigment deposition, chloasma, freckles, liver spots, etc. after sunburn, and is superior in terms of safety.

DETAILED DESCRIPTION OF THE INVENTION

The Pinon Negro, Cola de caballo, Piri-Piri, and Pinon Blanco extracts used in the present invention is a plant found on dry grassy plains and pastures in South America, particularly in the Andes. The extract used in the present invention is obtained by immersing or heat refluxing the whole plant of Pinon Negro including leaves, stems, fruits, etc. in an extraction solvent, followed by filtering and condensation. The extraction solvent used in the present invention can be any solvent which is normally used for extraction. Examples include alcohols such as methanol and ethanol, hydrated alcohols, and organic solvents such as acetone and ethyl acetate, and they can be used either independently or in combination.

In the present invention, the content of the Cola de caballo extract, Piri-Piri extract, Pinon Negro extract and Pinon Blanco on a dry basis, is 0.005 to 20.0 wt %, preferably 0.01 to 10.0 wt %, of the total endermic liniment. If it is less than 0.005 wt %, then the effects of the present invention cannot be sufficiently achieved, and if it is more than 20 wt %, then pharmaceutical preparation becomes difficult. Therefore, neither case is preferable. No significant increase in the effect is observed when using more than 10 wt %.

In addition to the essential ingredients described above, the endermic liniment of the present invention can contain, as necessary, those ingredients such as normally used in cosmetics, drugs, etc. in the form of an endermic liniment, including other whitening agents, humectants, antioxidants, oil-based ingredients, ultraviolet light absorbents, surfactants, thickeners, alcohols, powder ingredients, colorings, water-based ingredients, water and various skin nutrients.

Further, sequestering agents including disodium edetate, trisodium edetate, sodium citrate, sodium polyphosphate, sodium metaphosphate and gluconic acid, drugs including caffeine, tannin, verapamil, tranexamic acid and its derivatives, Glycyrrhiza extract, glabridin, various crude drugs, tocopherot acetate, glycyrrhizic acid and its derivatives or its salts, whitening agents including vitamin C, ascorbic acid phosphate magnesium, ascorbic acid glucoside, arbutin and kojic acid, and sugars including glucose, fructose, mannose, sucrose and trehalose can also be added.

The endermic liniment of the present invention can be in any form which is usually used for endermic liniment, including ointment, cream, emulsion, lotion, facial packs and bath additives. The present invention is described in detail below by referring to examples. The present invention is not limited to these examples. The blend ratios are in weight percent units. Before explaining the examples, the testing methods and the results of the melanin suppression effect, tyrosinase activity inhibition effect and whitening effect of the plant extract of the present invention are described.

Cola de caballo Extracts

1. Sample Preparation 50 g of stem and branch parts of Cola de caballo were immersed in ethanol at room temperature for a week. The extract solution was then concentrated to obtain 2.4 g of an ethanol extract. This extract was dissolved in DMSO to obtain a 1% solution, and this solution was diluted to adjust the concentration for the following experiments.

2. Cell Culture

B16 melanoma culture cells from mice were used. A culture was conducted in a $CO_2$ incubator (95% air and 5% carbon oxide) at 37° C. using Eagle's medium containing 10% FBS and theophylline (0.09 mg/ml). After 24 hours of culturing, the sample solution was added to it such that the final concentration (in dried extract) was $10^{-2}$ to $10^{-5}$ wt %. The culture was continued for 3 more days, and melanine production was visually evaluated and the tyrosinase activity inihibition effect was measured.

3. Visual Evaluation of the Amount of Melanin

A diffusion plate was placed on top of the lid of the well plate, and the amount of melanin in the cells was evaluated using an inverted microscope. The evaluation was compared with that of a sample with no added Cola de caballo extract (control sample). The results are shown in Table 1.

For a reference, the same testing was conducted on Nepeta japonica Maxim. (*Lamium album* L. subfamily, perilla family) extract which was already known to suppress melanin production. These results are also shown in Table 1. In the table, "toxicity" means there is cell toxicity.

Criteria:

○: White (amount of melanin)

Δ: Somewhat white (amount of melanin)

X: Control (amount of melanin)

4. Tyrosinase Activity Measurement

Before the measurement, the medium was removed, followed by washing twice with 100 microliters of PBS. 45 microliters of PBS containing 1% Triton X (surfactant from Rohm & Haas) was then added to each well. The plate was vibrated for 1 minute to thoroughly destroy the cell membranes, and the absorbance at 475 nm was measured using a microplate reader, which was defined as the absorbance at time 0 minutes. Quickly after this, 5 microliters of 10 mML-Dopa solution was added and the plate was transferred to an incubator kept at 37° C. to react for 60 minutes. The plate was vibrated for 1 minute and the absorbance (475 nm) at time 60 minutes was measured. The tyrosinase activity inhibition ratio (%) was defined as a decrease in the absorbance difference between time 0 minutes and time 60 minutes for the sample to which Cola de caballo extract was added compared with the absorbance difference between time 0 minutes and time 60 minutes for the sample to which Cola de caballo extract was not added. The results are shown in Table 1.

For a reference, the same testing was conducted on *Nepeta japonica* Maxim. extract which was already known to inhibit tyrosinase activity. These results are also shown in Table 1. In the table, "toxicity" means there is cell toxicity, and "-" indicates that no significant difference compared with the control was observed within 5%-level of significance.

TABLE 1

| Concentration (wt %) | Visual Evaluation of Melanin Production | | | | Tyrosinase Activity Activity Inhibition Ratio (%) | | | |
|---|---|---|---|---|---|---|---|---|
| | $10^{-5}$ | $10^{-4}$ | $10^{-3}$ | $10^{-2}$ | $10^{-5}$ | $10^{-4}$ | $10^{-3}$ | $10^{-2}$ |
| Cola de caballo extract | X | ○ | ○ | Δ | 24 | 28 | 38 | 56 |
| Nepeta japonica Maxim. extract | X | X | X | X | — | — | — | 55 |

5. Whitening Effect Testing 40 testees were exposed to summer sunlight for 4 hours (2 hours a day for 2 days) and the skin of an inner lateral part of their upper arm was used as the subject of the test. Beginning after 5 days from the day they were exposed to the sunlight, each sample was applied to this skin once in the morning and once in the afternoon for 4 weeks. The panel was divided into 5 groups with 8 persons in each group. Testing was conducted using the following formulations.

| Alcohol Phase | |
|---|---|
| 95% ethyl alcohol: | 55.0 wt % |
| Polyoxyethylene (25-mole) hardened castor oil ether | 2.0 |
| Antioxidant/preservative | Appropriate amount |
| Perfume | Appropriate amount |
| Drug | Specified in Table 2 |
| Water Phase | |
| Glycerine | 5.0 |
| Sodium hexamethaphosphate | Appropriate amount |
| Ion exchange water | Balance |

Preparation Method

The water phase and the alcohol phase were prepared separately and then mixed and solubilized.

Evaluation Method

The hypochromic effect after the application was evaluated based on the criteria below.

Criteria:

⊚: Very effective or effective on 80% or more of the testees

○: Very effective or effective on 50% to less than 80% of the testees

Δ: Very effective or effective on 30% to less than 50% testees

X: Very effective or effective on less than 30% of the testees

Samples were prepared with the blend compositions described in the aforementioned test method, and the drugs listed in Table 2 were used to compare the whitening effect. The results are shown in Table 2.

TABLE 2

| Drug | Blend Ratio (wt %) | Effect |
|---|---|---|
| Nothing added | — | X |
| Hydroquinone | 1.0 | Δ |
| Cola de caballo extract | 0.1 | ○ |
| Cola de caballo extract | 1.0 | ○ |
| Cola de caballo extract | 10.0 | ⊚ |

The Cola de caballo extracts in Table 2 were obtained by heated reduction of the whole plant of Cola de caballo in ethanol, followed by filtering and concentration/drying.

As clearly shown in Table 2, it was confirmed that the samples with Cola de caballo extract more effectively prevented excessive deposition of the melanin pigment and thus prevented darkening of the skin.

EXAMPLE 1

Cream Formula

| Stearic acid | 5.0 wt % |
|---|---|
| Stearyl alcohol | 4.0 |
| Isopropyl myristate | 18.0 |
| Glycerine monostearic ester | 3.0 |

-continued

| | |
|---|---|
| Propylene glycol | 10.0 |
| Cola de caballo methanol extract | 0.01 |
| Caustic potash | 0.2 |
| Sodium hydrogen sulfite | 0.01 |
| Preservative | Appropriate amount |
| Perfume | Appropriate amount |
| Ion exchange water | Balance |

Preparation Method

Propylene glycol, the Cola de caballo extract and caustic potash were added to the ion exchange water and the mixture was heated to-and kept at 70° C. (water phase). Other ingredients were mixed, then heat-melted and the temperature was kept at 70° C. (oil phase). The oil phase was gradually added to the water phase, and after all of it had been added, the temperature was kept at that temperature to allow the mixture to react. Finally, the mixture was homogeneously emulsified by a homo-mixer and cooled to 30° C. while being thoroughly stirred.

EXAMPLE 2

Cream Formula

| | |
|---|---|
| Stearic acid | 2.0 wt % |
| Stearyl alcohol | 7.0 |
| Hydrated lanolin | 2.0 |
| Squalane | 5.0 |
| 2-octyldodecyl alcohol | 6.0 |
| Polyoxyethylene (25-mole) cetyl alcohol ether | 3.0 |
| Glycerine monostearic ester | 2.0 |
| Propylene glycol | 5.0 |
| Cola de caballo extract | 0.05 |
| Sodium hydrogen sulfite | 0.03 |
| Ethyl paraben | 0.3 |
| Perfume | Appropriate amount |
| Ion exchange water | Balance |

Preparation Method

Propylene glycol was added to the ion exchange water and the mixture was heated to and kept at 70° C. (water phase). Other ingredients were mixed, then heat-melted and the temperature was kept at 70° C. (oil phase). The oil phase was added to the water phase, and after pre-emulsification, the mixture was homogeneously emulsified by a homo-mixer and cooled to 30° C. while being thoroughly stirred.

EXAMPLE 3

Cream Formula

| | |
|---|---|
| Solid paraffin | 5.0 wt % |
| Bees wax | 10.0 |
| Vaseline | 15.0 |
| Liquid paraffin | 41.0 |
| Glycerine monostearic ester | 2.0 |
| Polyoxyethylene (20-mole) sorbitan monolauric ester | 2.0 |
| Soap powder | 0.1 |
| Borax | 0.2 |
| Cola de caballo acetone extract | 0.05 |
| Cola de caballo ethanol extract | 0.05 |
| Sodium hydrogen sulfite | 0.03 |
| Ethyl paraben | 0.3 |
| Perfume | Appropriate amount |
| Ion exchange water | Balance |

Preparation Method

Soap powder and borax were added to the ion exchange water and the mixture was heated to and kept at 70° C. (water phase). Other ingredients were mixed, then heat-melted and the temperature was kept at 70° C. (oil phase). The oil phase was gradually added to the water phase while stirring was conducted to allow the reaction to occur. When the reaction was complete, the mixture was homogeneously emulsified by a homo-mixer and then cooled to 30° C. while being thoroughly stirred.

EXAMPLE 4

Emulsion Formula

| | |
|---|---|
| Stearic acid | 2.5 wt % |
| Cetyl alcohol | 1.5 |
| Vaseline | 5.0 |
| Liquid paraffin | 10.0 |
| Polyoxyethylene (10-mole) monooleic ester | 2.0 |
| Polyethylene glycol 1500 | 3.0 |
| Triethanol amine | 1.0 |
| Carboxyvinyl polymer (Product name: Carbomer 941 from B.F. Goodrich Chemical Company) | 0.05 |
| Cola de caballo ethyl acetate extract | 0.01 |
| Sodium hydrogen sulfite | 0.01 |
| Ethyl paraben | 0.3 |
| Perfume | Appropriate amount |
| Ion exchange water | Balance |

Preparation Method

Carboxyvinyl polymer was dissolved in a small amount of the ion exchange water (A phase). Polyethylene glycol 1500 and triethanol amine were added to and heat-dissolved in the rest of the ion exchange water, and the temperature was kept at 70° C. (water phase). Other ingredients were mixed, then heat-melted and the temperature was kept at 70° C. (oil phase). The oil phase was added to the water phase, and, after pre-emulsification, the A phase was added and the mixture was homogeneously emulsified by a homo-mixer and cooled to 30° C. while being thoroughly stirred.

EXAMPLE 5

Emulsion Formula

| | |
|---|---|
| Microcrystalline wax | 1.0 wt % |
| Bees wax | 2.0 |
| Lanolin | 20.0 |
| Liquid paraffin | 10.0 |
| Squalene | 5.0 |
| Sorbitan sesquioleic ester | 4.0 |
| Polyoxyethylene (20-mole) sorbitan monooleic ester | 1.0 |
| Propylene glycol | 7.0 |
| Cola de caballo acetone extract | 10.0 |
| Sodium hydrogen sulfite | 0.03 |
| Ethyl paraben | 0.3 |
| Perfume | Appropriate amount |
| Ion exchange water | Balance |

Preparation Method

Propylene glycol was added to the ion exchange water and the mixture was heated to and kept at 70° C. (water phase). Other ingredients were mixed, then heat-melted and the temperature was kept at 70° C. (oil phase). The oil phase was gradually added to the water phase while stirring was conducted, and the mixture was homogeneously emulsified by a homo-mixer and then cooled to 30° C. while being thoroughly stirred.

EXAMPLE 6

Jelly Formula

| | |
|---|---|
| 95% ethyl alcohol | 10.0 wt % |
| Dipropylene glycol | 15.0 |
| Polyoxyethylene (50-mole) oleyl alcohol ether | 2.0 |
| Carboxyvinyl polymer (Product name: Carbomer 940 from B.F. Goodrich Chemical company) | 1.0 |
| Caustic soda | 0.15 |
| L-arginine | 0.1 |
| Cola de caballo 50% ethanol aqueous solution extract | 7.0 |
| Sodium 2-hydroxy-4-methoxybenzophenone-sulfonate | 0.05 |
| Ethylenediamine-tetraacetic acid trisodium dihydrate | 0.05 |
| Methyl paraben | 0.2 |
| Perfume | Appropriate amount |
| Ion exchange water | Balance |

Preparation Method

Carbomer 940 was homogeneously dissolved in the ion exchange water. Cola de caballo 50% ethanol aqueous solution extract and polayoxyethylene (50-mole) oleyl alcohol ether were dissolved in 95% ethanol and this mixture was added to the water phase. Other ingredients were then added, and the mixture was neutralized and thickened with caustic soda and L-arginine.

EXAMPLE 7

Essence Formula

| | |
|---|---|
| Phase A | |
| Ethyl alcohol (95%) | 10.0 wt % |
| Polyoxyethylene (20-mole) octyl dodecanol | 1.0 |
| Pantothenyl ethyl ether | 0.1 |
| Cola de caballo methanol extract | 1.5 |
| Methyl paraben | 0.15 |
| Phase B | |
| Potassium hydroxide | 0.1 |
| Phase C | |
| Glycerine | 5.0 |
| Dipropylene glycol | 10.0 |
| Sodium hydrogen sulfite | 0.03 |
| Carboxyvinyl polymer (Product name: Carbomer 940 from B.F. Goodrich Chemical Company) | 0.2 |
| Purified Water | Balance |

Preparation Method

The Phase A and Phase C were independently dissolved homogeneously, and then the A phase was added to Phase C and solubilized. The Phase B was then added, and finally containers were filled.

EXAMPLE 8

Facial Pack Formula

| | |
|---|---|
| Phase A | |
| Dipropylene glycol | 5.0 wt % |
| Polyoxyethylene (60-mole) hardened castor oil | 5.0 |
| Phase B | |
| Cola de caballo methanol extract | 0.01 |
| Olive oil | 5.0 |
| Tocopherol acetate | 0.2 |
| Ethyl paraben | 0.2 |
| Perfume | 0.2 |
| Phase C | |
| Sodium hydrogen sulfite | 0.03 |
| Polyvinyl alcohol (Degree of saponification 90, degree of polymerization 2,000) | 13.0 |
| Ethanol | 7.0 |
| Purified water | Balance |

Preparation Method

The A, B and C phases were independently dissolved homogeneously, and then Phase B was added to Phase A and solubilized. Phase C was then added to this, and finally containers were filled.

EXAMPLE 9

Solid Foundation Formula

| | |
|---|---|
| Talc | 43.1 wt % |
| Kaolin | 15.0 |
| Sericite | 10.0 |
| Zinc flower | 7.0 |
| Titanium dioxide | 3.8 |
| Yellow iron oxide | 2.9 |
| Black iron oxide | 0.2 |
| Squalene | 8.0 |
| Isostearic acid | 4.0 |
| POE sorbitan monooleate | 3.0 |
| Isocetyl octate | 2.0 |
| Cola de caballo ethanol extract | 1.0 |
| Preservative | Appropriate amount |
| Perfume | Appropriate amount |

Preparation Method

The powder ingredients, i.e. from talc to black iron oxide, were thoroughly mixed by a blender, and the oil-based ingredients, i.e. from squalene to isocetyl octate, Cola de caballo ethanol extract, the preservative and the perfume were added to this. After a thorough kneading, the product was filled into a container and molded.

EXAMPLE 10

Emulsified Foundation (cream type) Formula

| | |
|---|---|
| Powder Portion | |
| Titanium dioxide | 10.3 wt % |
| Sericite | 5.4 |
| Kaolin | 3.0 |
| Yellow iron oxide | 0.8 |
| Red iron oxide | 0.3 |
| Black iron oxide | 0.2 |
| Oil Phase | |
| Decamethylpentasiloxane | 11.5 |
| Liquid paraffin | 4.5 |
| Polyoxyethylene modified dimethylpolysiloxane | 4.0 |
| Water Phase | |
| Purified water | 50.0 |
| 1,3-butylene glycol | 4.5 |

| | |
|---|---|
| Cola de caballo ethanol extract | 1.5 |
| Sorbitan sesquioleic ester | 3.0 |
| Preservative | Appropriate amount |
| Perfume | Appropriate amount |

Preparation Method

After heating and stirring the water phase, the powder portion, thoroughly mixed and crushed, was added to it and the mixture was treated with a homo-mixer. The heat-mixed oil phase was then added to this mixture and the resulting mixture was treated with a homo-mixer. Finally, the perfume was added while the mixture was stirred and the temperature was lowered to room temperature.

Piri-Piri Extracts

1. Sample Preparation 50 g of stem and branch parts of Piri-Piri were immersed in ethanol at room temperature for a week. The extract solution was then concentrated to obtain 1.8 g of an ethanol extract. This extract was dissolved in DMSO to obtain a 1% solution, and this solution was diluted to adjust the concentration for the following experiments.

2. Cell Culture

B16 melanoma culture cells from mice were used. A culture was conducted in a CO2 incubator (95% air and 5% carbon oxide) at 37° C. using Eagle's medium containing 10% FBS and theophylline (0.09 mg/ml). After 24 hours of culturing, the sample solution was added to it such that the final concentration (in dried extract) was $10^{-2}$ to $10^{-5}$ wt %. The culture was continued for 3 more days, and melanine production was visually evaluated and the tyrosinase activity inihibition effect was measured.

3. Visual Evaluation of the Amount of Melanin

A diffusion plate was placed on top of the lid of the well plate, and the amount of melanin in the cells was evaluated using an inverted microscope. The evaluation was compared with that of a sample with no added Piti-Piti extract (control sample). The results are shown in Table 3.

For a reference, the same testing was conducted on Nepeta japonica Maxim. (Lamium album L. subfamily, perilla family) extract which was already known to suppress melanin production. These results are also shown in Table 3. In the table, "toxicity" means there is cell toxicity.

Criteria:

○: White (amount of melanin)

Δ: Somewhat white (amount of melanin)

X: Control (amount of melanin)

4. Tyrosinase Activity Measurement

Before the measurement, the medium was removed, followed by washing twice with 100 microliters of PBS. 45 microliters of PBS containing 1% Triton X (surfactant from Rohm & Haas) was then added to each well. The plate was vibrated for 1 minute to thoroughly destroy the cell membranes, and the absorbance at 475 nm was measured using a microplate reader, which was defined as the absorbance at time 0 minutes. Quickly after this, 5 microliters of 10 mML-Dopa solution was added and the plate was 5 transferred to an incubator kept at 37° C. to react for 60 minutes. The plate was vibrated for 1 minute and the absorbance (475 nm) at time 60 minutes was measured. The tyrosinase activity inhibition ratio (%) was defined as a decrease in the absorbance difference between time 0 minutes and time 60 minutes for the sample to which Piri-Piri extract was added compared with the absorbance difference between time 0 minutes and time 60 minutes for the sample to which Piti-Piti extract was not added. The results are shown in Table 3.

For a reference, the same testing was conducted on Nepeta japonica Maxim. extract which was already known to inhibit tyrosinase activity. These results are also shown in Table 3. In the table, "toxicity" means there is cell toxicity, and "-" indicates that no significant difference compared with the control was observed within 5%-level of significance.

TABLE 3

| Concentration (wt %) | Visual Evaluation of Melanin Production | | | | Tyrosinase Activity Activity Inhibition Ratio (%) | | | |
|---|---|---|---|---|---|---|---|---|
| | $10^{-5}$ | $10^{-4}$ | $10^{-3}$ | $10^{-2}$ | $10^{-5}$ | $10^{-4}$ | $10^{-3}$ | $10^{-2}$ |
| Piri-Piri extract | ○ | Δ | ○ | Toxicity | — | — | 72 | Toxicity |
| Nepeta japonica Maxim. extract | X | X | X | X | — | — | — | 55 |

5. Whitening Effect Testing

Test Method 40 testees were exposed to summer sunlight for 4 hours (2 hours a day for 2 days) and the skin of an inner lateral part of their upper arm was used as the subject of the test. Beginning after 5 days From the day they were exposed to the sunlight, each sample was applied to this skin once in the morning and once in the afternoon for 4 weeks. The panel was divided into 5 groups with 8 persons in each group. Testing was conducted using the following formulations.

| Alcohol Phase | |
|---|---|
| 95% ethyl alcohol | 55.0 wt % |
| Polyoxyethylene (25-mole) hardened castor oil ether | 2.0 |
| Antioxidant/preservative | Appropriate amount |
| Perfume | Appropriate amount |
| Drug (specified in Table 2) | |
| Water Phase | |
| Glycerine | 5.0 |
| Sodium hexamethaphosphate | Appropriate amount |
| Ion exchange water | Balance |

Preparation Method

The water phase and the alcohol phase were prepared separately and then mixed and solubilized.

Evaluation Method

The hypochromic effect after the application was evaluated based on the criteria below.

Criteria:

⊙: Very effective or effective on 80% or more of the testees

○: Very effective or effective on 50% to less than 80% of the testees

Δ: Very effective or effective on 30% to less than 50% testees

X: Very effective or effective on less than 30% of the testees

Samples were prepared with the blend compositions described in the aforementioned test method, and the drugs listed in Table 4 were used to compare the whitening effect. The results are shown in Table 4.

TABLE 4

| Drug | Blend Ratio (wt %) | Effect |
| --- | --- | --- |
| Nothing added | — | X |
| Hydroquinone | 1.0 | Δ |
| Piri-Piri extract | 0.1 | ○ |
| Piri-Piri extract | 1.0 | ○ |
| Piri-Piri extract | 10.0 | ⊙ |

The Piri-Piri extracts in Table 4 were obtained by heated reduction of the whole plant of Piri-Piri in ethanol, followed by filtering and concentration/drying.

As clearly shown in Table 4, it was confirmed that the samples with Piri-Piri extract more effectively prevented excessive depositio of the melanin pigment and thus prevented darkening of the skin.

EXAMPLE 11

Cream Formula

| | |
| --- | --- |
| Stearic acid | 5.0 wt % |
| Stearyl alcohol | 4.0 |
| Isopropyl myristate | 18.0 |
| Glycerine monostearic ester | 3.0 |
| Propylene glycol | 10.0 |
| Piri-Piri methanol extract | 0.01 |
| Caustic potash | 0.2 |
| Sodium hydrogen sulfite | 0.01 |
| Preservative | Appropriate amount |
| Perfume | Appropriate amount |
| Ion exchange water | Balance |

Preparation Method

Propylene glycol, the Piri-Piri extract and caustic potash were added to the ion exchange water and the mixture was heated to and kept at 70° C. (water phase). Other ingredients were mixed, then heat-melted and the temperature was kept at 70° C. (oil phase). The oil phase was gradually added to the water phase, and after all of it had been added, the temperature was kept at that temperature to allow the mixture to react. Finally, the mixture was homogeneously emulsified by a homo-mixer and cooled to 30° C. while being thoroughly stirred.

EXAMPLE 12

Cream Formula

| | |
| --- | --- |
| Stearic acid | 2.0 wt % |
| Stearyl alcohol | 7.0 |
| Hydrated lanolin | 2.0 |
| Squalene | 5.0 |
| 2-octyldodecyl alcohol | 6.0 |
| Polyoxyethylene (25-mole) cetyl alcohol ether | 3.0 |
| Glycerine monostearic ester | 2.0 |
| Propylene glycol | 5.0 |
| Piri-Piri extract | 0.05 |
| Sodium hydrogen sulfite | 0.03 |
| Ethyl paraben | 0.3 |
| Perfume | Appropriate amount |
| Ion exchange water | Balance |

Preparation Method

Propylene glycol was added to the ion exchange water and the mixture was heated to and kept at 70° C. (water phase). Other ingredients were mixed, then heat-melted and the temperature was kept at 70° C. (oil phase). The oil phase was added to the water phase, and after pre-emulsification, the mixture was homogeneously emulsified by a homo-mixer and cooled to 30° C. while being thoroughly stirred.

EXAMPLE 13

Cream Formula

| | |
| --- | --- |
| Solid paraffin | 5.0 wt % |
| Bees wax | 10.0 |
| Vaseline | 15.0 |
| Liquid paraffin | 41.0 |
| Glycerine monostearic ester | 2.0 |
| Polyoxyethylene (20-mole) sorbitan monolauric ester | 2.0 |
| Soap powder | 0.1 |
| Borax | 0.2 |
| Piri-Piri acetone extract | 0.05 |
| Piri-Piri ethanol extract | 0.05 |
| Sodium hydrogen sulfite | 0.03 |
| Ethyl paraben | 0.3 |
| Perfume | Appropriate amount |
| Ion exchange water | Balance |

Preparation Method

Soap powder and borax were added to the ion exchange water and the mixture was heated to and kept at 70° C. (water phase). Other ingredients were mixed, then heat-melted and the temperature was kept at 70° C. (oil phase). The oil phase was gradually added to the water phase while stirring was conducted to allow the reaction to occur. When the reaction was complete, the mixture was homogeneously emulsified by a homo-mixer and then cooled to 30° C. while being thoroughly stirred.

EXAMPLE 14

Emulsion Formula

| | |
| --- | --- |
| Stearic acid | 2.5 wt % |
| Cetyl alcohol | 1.5 |
| Vaseline | 5.0 |
| Liquid paraffin | 10.0 |
| Polyoxyethylene (10-mole) monooleic ester | 2.0 |
| Polyethylene glycol 1500 | 3.0 |
| Triethanol amine | 1.0 |
| Carboxyvinyl polymer (Product name: Carbomer 941 from B. F. Goodrich Chemical company) | 0.05 |
| Piri-Piri ethyl acetate extract | 0.01 |
| Sodium hydrogen sulfite | 0.01 |
| Ethyl paraben | 0.3 |
| Perfume | Appropriate amount |
| Ion exchange water | Balance |

Preparation Method

Carboxyvinyl polymer was dissolved in a small amount of the ion exchange water (A phase). Polyethylene glycol 1500 and triethanol amine were added to and heat-dissolved in the rest of the ion exchange water, and the temperature was kept at 70° C. (water phase). Other ingredients were mixed, then heat-melted and the temperature was kept at 70° C. (oil phase). The oil phase was added to the water phase, and, after pre-emulsification, the A phase was added and the mixture was homogeneously emulsified by a homo-mixer and cooled to 30° C. while being thoroughly stirred.

EXAMPLE 15

Emulsion Formula

| | |
|---|---|
| Microcrystalline wax | 1.0 wt % |
| Bees wax | 2.0 |
| Lanolin | 20.0 |
| Liquid paraffin | 10.0 |
| Squalene | 5.0 |
| Sorbitan sesquioleic ester | 4.0 |
| Polyoxyethylene (20-mole) sorbitan monooleic ester | 1.0 |
| Propylene glycol | 7.0 |
| Piri-Piri acetone extract | 10.0 |
| Sodium hydrogen sulfite | 0.03 |
| Ethyl paraben | 0.3 |
| Perfume | Appropriate amount |
| Ion exchange water | Balance |

Preparation Method

Propylene glycol was added to the ion exchange water and the mixture was heated to and kept at 70° C. (water phase). Other ingredients were mixed, then heat-melted and the temperature was kept at 70° C. (oil phase). The oil phase was gradually added to the water phase while stirring was conducted, and the mixture was homogeneously emulsified by a homo-mixer and then cooled to 30° C while being thoroughly stirred.

EXAMPLE 16

Jelly Formula

| | |
|---|---|
| 95% ethyl alcohol | 10.0 wt % |
| Dipropylene glycol | 15.0 |
| Polyoxyethylene (50-mole) oleyl alcohol ether | 2.0 |
| Carboxyvinyl polymer (Product name: Carbomer 940 from B. F. Goodrich Chemical company) | 1.0 |
| Caustic soda | 0.15 |
| L-arginine | 0.1 |
| Piri-Piri 50% ethanol aqueous solution extract | 7.0 |
| Sodium 2-hydroxy-4-methoxybenzo-phenonesulfonate | 0.05 |
| Ethylenediamine-tetraacetic acid trisodium dihydrate | 0.05 |
| Methyl paraben | 0.2 |
| Perfume | Appropriate amount |
| Ion exchange water | Balance |

Preparation Method

Carbomer 940 was homogeneously dissolved in the ion exchange water. Piri-Piri 50% ethanol aqueous solution extract and polyoxyethylene (50-mole) oleyl alcohol ether were dissolved in 95% ethanol and this mixture was added to the water phase. Other ingredients were then added, and the mixture was neutralized and thickened with caustic soda and L-arginine.

EXAMPLE 17

Essence Formula

| A Phase | |
|---|---|
| Ethyl alcohol (95%) | 10.0 wt % |
| Polyoxyethylene (20-mole) octyl dodecanol | 1.0 |
| Pantothenyl ethyl ether | 0.1 |
| Piri-Piri methanol extract | 1.5 |
| Methyl paraben | 0.15 |
| B Phase | |
| Potassium hydroxide | 0.1 |
| C Phase | |
| Glycerine | 5.0 |
| Dipropylene glycol | 10.0 |
| Sodium hydrogen sulfite | 0.03 |
| Carboxyvinyl polymer (Product name: Carbomer 940 from B. F. Goodrich Chemical company) | 0.2 |
| Purified water | Balance |

Preparation Method

The A phase and the C phase were independently dissolved homogeneously, and then the A phase was added to the C phase and solubilized. The B phase was then added, and finally containers were filled.

EXAMPLE 18

Facial Pack Formula

| A Phase | |
|---|---|
| Dipropylene glycol | 5.0 wt % |
| Polyoxyethylene (60-mole) hardened castor oil | 5.0 |
| B Phase | |
| Piri-Piri methanol extract | 0.01 |
| Olive oil | 5.0 |
| Tocopherol acetate | 0.2 |
| Ethyl paraben | 0.2 |
| Perfume | 0.2 |
| C Phase | |
| Sodium hydrogen sulfite | 0.03 |
| Polyvinyl alcohol (Degree of saponification 90, degree of polymerization 2,000) | 13.0 |
| Ethanol | 7.0 |
| Purified water | Balance |

Preparation Method

The A, B and C phases were independently dissolved homogeneously, and then the B phase was added to the A phase and solubilized. The C phase was then added to this, and finally containers were filled.

EXAMPLE 19

Solid Foundation Formula

| | |
|---|---|
| Talc | 43.1 wt % |
| Kaolin | 15.0 |
| Sericite | 10.0 |
| Zinc flower | 7.0 |
| Titanium dioxide | 3.8 |
| Yellow iron oxide | 2.9 |
| Black iron oxide | 0.2 |
| Squalene | 8.0 |
| Isostearic acid | 4.0 |
| POE sorbitan monooleate | 3.0 |
| Isocetyl octate | 2.0 |
| Piri-Piri ethanol extract | 1.0 |
| Preservative | Appropriate amount |
| Perfume | Appropriate amount |

Preparation Method

The powder ingredients, i.e. from talc to black iron oxide, were thoroughly mixed by a blender, and the oil-based ingredients, i.e. from squalene to isocetyl octate, Piri-Piri ethanol extract, the preservative and the perfume were added to this. After a thorough kneading, the product was filled into a container and molded.

EXAMPLE 20

Emulsified Foundation (cream type) Formula

| Powder Portion | |
| --- | --- |
| Titanium dioxide | 10.3 wt % |
| Sericite | 5.4 |
| Kaolin | 3.0 |
| Yellow iron oxide | 0.8 |
| Red iron oxide | 0.3 |
| Black iron oxide | 0.2 |
| Oil Phase | |
| Decamethylpentasiloxane | 11.5 |
| Liquid paraffin | 4.5 |
| Polyoxyethylene modified dimethylpolysiloxane | 4.0 |
| Water Phase | |
| Purified water | 50.0 |
| 1,3-butylene glycol | 4.5 |
| Piri-Piri ethanol extract | 1.5 |
| Sorbitan sesquioleic ester | 3.0 |
| Preservative | Appropriate amount |
| Perfume | Appropriate amount |

Preparation Method

After heating and stirring the water phase, the powder portion, thoroughly mixed and crushed, was added to it and the mixture was treated with a homo-mixer. The heat-mixed oil phase was then added to this mixture and the resulting mixture was treated with a homo-mixer. Finally, the perfume was added while the mixture was stirred and the temperature was lowered to room temperature.

Pinon Negro Extract

1. Sample Preparation 50 g of stem and branch parts of Pinon Negro were immersed in ethanol at room temperature for a week. The extract solution was then concentrated to obtain 2.7 g of an ethanol extract. This extract was dissolved in DMSO to obtain a 1% solution, and this solution was diluted to adjust the concentration for the following experiments.

2. Cell Culture

B16 melanoma culture cells from mice were used. A culture was conducted in a CO2 incubator (95% air and 5% carbon oxide) at 37° C. using Eagle's medium containing 10% FBS and theophylline (0.09 mg/ml). After 24 hours of culturing, the sample solution was added to it such that the final concentration (in dried extract) was $10^{-2}$ to $10^{-5}$ wt %. The culture was continued for 3 more days, and melanine production was visually evaluated and the tyrosinase activity inihibition effect was measured.

3. Visual Evaluation of the Amount of Melanin

A diffusion plate was placed on top of the lid of the well plate, and the amount of melanin in the cells was evaluated using an inverted microscope. The evaluation was compared with that of a sample with no added Pinon Negro extract (control sample). The results are shown in Table 5.

For a reference, the same testing was conducted on Nepeta japonica Maxim. (Lamium album L. subfamily, perilla family) extract which was already known to suppress melanin production. These results are also shown in Table 5. In the table, "toxicity" means there is cell toxicity.

Criteria:

○: White (Amount of Melanin)

Δ: Somewhat white (amount of melanin)

X: Control (amount of melanin)

4. Tyrosinase Activity Measurement

Before the measurement, the medium was removed, followed by washing twice with 100 microliters of PBS. 45 microliters of PBS containing 1% Triton X (surfactant from Rohm & Haas) was then added to each well. The plate was vibrated for 1 minute to thoroughly destroy the cell membranes, and the absorbance at 475 nm was measured using a microplate reader, which was defined as the absorbance at time 0 minutes. Quickly after this, 5 microliters of 10 mML-Dopa solution was added and the plate was transferred to an incubator kept at 37° C. to react for 60 minutes. The plate was vibrated for 1 minute and the absorbance (475 nm) at time 60 minutes was measured. The tyrosinase activity inhibition ratio (%) was defined as a decrease in the absorbance difference between time 0 minutes and time 60 minutes for the sample to which Pinon Negro extract was added compared with the absorbance difference between time 0 minutes and time 60 minutes for the sample to which Pinon Negro extract was not added. The results are shown in Table 5.

For a reference, the same testing was conducted on Nepeta japonica Maxim. extract which was already known to inhibit tyrosinase activity. These results are a shown in Table 5. In the table, "toxicity" means there is cell toxicity, and "-" indicates that no significant difference compared with the control was observed within 5%-level of significance.

TABLE 5

| Concentration (wt %) | Visual Evaluation of Melanin Production | | | | Tyrosinase Activity Activity Inhibition Ratio (%) | | | |
| --- | --- | --- | --- | --- | --- | --- | --- | --- |
| | $10^{-5}$ | $10^{-4}$ | $10^{-3}$ | $10^{-2}$ | $10^{-5}$ | $10^{-4}$ | $10^{-3}$ | $10^{-2}$ |
| Pinon Negro extract | ○ | ○ | ○ | ○ | 40 | 42 | 61 | 85 |
| Nepeta japonica Maxim. extract | X | X | X | X | — | — | — | 55 |

5. Whitening Effect Testing

Test Method 40 testees were exposed to summer sunlight for 4 hours (2 hours a day for 2 days) and the skin of an inner lateral part of their upper arm was used as the subject of the test. Beginning after 5 days from the day they were exposed to the sunlight, each sample was applied to this skin once in the morning and once in the afternoon for 4 weeks. The panel was divided into 5 groups with 8 persons in each group. Testing was conducted using the following formulations.

| Alcohol Phase | |
| --- | --- |
| 95% ethyl alcohol | 55.0 wt % |
| Polyoxyethylene (25-mole) hardened castor oil ether | 2.0 |
| Antioxidant/preservative | Appropriate amount |
| Perfume | Appropriate amount |
| Drug (specified in Table 6) | |

| Water Phase | |
|---|---|
| Glycerine | 5.0 |
| Sodium hexamethaphosphate | Appropriate amount |
| Ion exchange water | Balance |

Preparation Method

The water phase and the alcohol phase were prepared separately and then mixed and solubilized.

Evaluation Method

The hypochromic effect after the application was evaluated based on the criteria below.

Criteria:

⊙: Very effective or effective on 80% or more of the testees

○: Very effective or effective on 50% to less than 80% of the testees

Δ: Very effective or effective on 30% to less than 50% testees

X: Very effective or effective on less than 30% of the testees

Samples were prepared with the blend compositions described in the aforementioned test method, and the drugs listed in Table 6 were used to compare the whitening effect. The results are shown in Table 6.

TABLE 6

| Drug | Blend Ratio (%) | Effect |
|---|---|---|
| Nothing Added | — | X |
| Hydroquinone | 1.0 | Δ |
| Pinon Negro extract | 0.1 | ○ |
| Pinon Negro extract | 1.0 | ○ |
| Pinon Negro extract | 10.0 | ⊙ |

The Pinon Negro extracts in Table 6 were obtained by heated reduction of the whole plant of Pinon Negro in ethanol, followed by filtering and concentration/drying.

As clearly shown in Table 6, it was confirmed that the samples with Pinon Negro extract more effectively prevented excessive deposition of the melanin pigment and thus prevented darkening of the skin.

EXAMPLE 21

Cream Formula

| Stearic acid | 5.0 wt % |
|---|---|
| Stearyl alcohol | 4.0 |
| Isopropyl myristate | 18.0 |
| Glycerine monostearic ester | 3.0 |
| Propylene glycol | 10.0 |
| Pinon Negro methanol extract | 0.01 |
| Caustic potash | 0.2 |
| Sodium hydrogen sulfite | 0.01 |
| Preservative | Appropriate amount |
| Perfume | Appropriate amount |
| Ion exchange water | Balance |

Preparation Method

Propylene glycol, the Pinon Negro extract and caustic potash were added to the ion exchange water and the mixture was heated to and kept at 70° C. (water phase). Other ingredients were mixed, then heat-melted and the temperature was kept at 70° C. (oil phase). The oil phase was gradually added to the water phase, and after all of it had been added, the temperature was kept at that temperature to allow the mixture to react. Finally, the mixture was homogeneously emulsified by a homo-mixer and cooled to 30° C. while being thoroughly stirred.

EXAMPLE 22

Cream Formula

| Stearic acid | 2.0 wt % |
|---|---|
| Stearyl alcohol | 7.0 |
| Hydrated lanolin | 2.0 |
| Squalene | 5.0 |
| 2-octyldodecyl alcohol | 6.0 |
| Polyoxyethylene (25-mole) cetyl alcohol ether | 3.0 |
| Glycerine monostearic ester | 2.0 |
| Propylene glycol | 5.0 |
| Pinon Negro extract | 0.05 |
| Sodium hydrogen sulfite | 0.03 |
| Ethyl paraben | 0.3 |
| Perfume | Appropriate amount |
| Ion exchange water | Balance |

Preparation Method

Propylene glycol was added to the ion exchange water and the mixture was heated to and kept at 70° C. (water phase). Other ingredients were mixed, then heat-melted and the temperature was kept at 70° C. (oil phase). The oil phase was added to the water phase, and after pre-emulsification, the mixture was homogeneously emulsified by a homo-mixer and cooled to 30° C. while being thoroughly stirred.

EXAMPLE 23

Cream Formula

| Solid paraffin | 5.0 wt % |
|---|---|
| Bees wax | 10.0 |
| Vaseline | 15.0 |
| Liquid paraffin | 41.0 |
| Glycerine monostearic ester | 2.0 |
| Polyoxyethylene (20-mole) sorbitan monolauric ester | 2.0 |
| Soap powder | 0.1 |
| Borax | 0.2 |
| Pinon Negro acetone extract | 0.05 |
| Pinon Negro ethanol extract | 0.05 |
| Sodium hydrogen sulfite | 0.03 |
| Ethyl paraben | 0.3 |
| Perfume | Appropriate amount |
| Ion exchange water | Balance |

Preparation Method

Soap powder and borax were added to the ion exchange water and the mixture was heated to and kept at 70° C. (water phase). Other ingredients were mixed, then heat-melted and the temperature was kept at 70° C. (oil phase). The oil phase was gradually added to the water phase while stirring was conducted to allow the reaction to occur. When the reaction was complete, the mixture was homogeneously emulsified by a homo-mixer and then cooled to 30° C. while being thoroughly stirred.

EXAMPLE 24

Emulsion Formula

| Stearic acid | 2.5 wt % |
|---|---|
| Cetyl alcohol | 1.5 |
| Vaseline | 5.0 |
| Liquid paraffin | 10.0 |

-continued

| | |
|---|---|
| Polyoxyethylene (10-mole) monooleic ester | 2.0 |
| Polyethylene glycol 1500 | 3.0 |
| Triethanol amine | 1.0 |
| Carboxyvinyl polymer (Product name: Carbomer 941 from B. F. Goodrich Chemical company) | 0.05 |
| Pinon Negro ethyl acetate extract | 0.01 |
| Sodium hydrogen sulfite | 0.01 |
| Ethyl paraben | 0.3 |
| Perfume | Appropriate amount |
| Ion exchange water | Balance |

Preparation Method

Carboxyvinyl polymer was dissolved in a small amount of the ion exchange water (A phase). Polyethylene glycol 1500 and triethanol amine were added to and heat-dissolved in the rest of the ion exchange water, and the temperature was kept at 70° C. (water phase). Other ingredients were mixed, then heat-melted and the temperature was kept at 70° C. (oil phase). The oil phase was added to the water phase, and, after pre-emulification, the A phase was added and the mixture was homogeneously emulsified by a homo-mixer and cooled to 30° C. while being thoroughly stirred.

EXAMPLE 25

Emulsion Formula

| | |
|---|---|
| Microcrystalline wax | 1.0 wt % |
| Bees wax | 2.0 |
| Lanolin | 20.0 |
| Liquid paraffin | 10.0 |
| Squalene | 5.0 |
| Sorbitan sesquioleic ester | 4.0 |
| Polyoxyethylene (20-mole) sorbitan monooleic ester | 1.0 |
| Propylene glycol | 7.0 |
| Pinon Negro acetone extract | 10.0 |
| Sodium hydrogen sulfite | 0.03 |
| Ethyl paraben | 0.3 |
| Perfume | Appropriate amount |
| Ion exchange water | Balance |

Preparation Method

Propylene glycol was added to the ion exchange water and the mixture was heated to and kept at 70° C. (water phase). Other ingredients were mixed, then heat-melted and the temperature was kept at 70° C. (oil phase). The oil phase was gradually added to the water phase while stirring was conducted, and the mixture was homogeneously emulsified by a homo-mixer and then cooled to 30° C. while being thoroughly stirred.

EXAMPLE 26

Jelly Formula

| | |
|---|---|
| 95% ethyl alcohol | 10.0 wt % |
| Dipropylene glycol | 15.0 |
| Polyoxyethylene (50-mole) oleyl alcohol ether | 2.0 |
| Carboxyvinyl polymer (Product name: Carbomer 940 from B.F. Goodrich Chemical company) | 1.0 |
| Caustic soda | 0.15 |
| L-arginine | 0.1 |
| Pinon Negro 50% ethanol aqueous solution extract | 7.0 |
| Sodium 2-hydroxy-4-methoxybenzophenone- | 0.05 |
| sulfonate | |
| Ethylenediamine-tetraacetic acid trisodium dihydrate | 0.05 |
| Methyl paraben | 0.2 |
| Perfume | Appropriate amount |
| Ion exchange water | Balance |

Preparation Method

Carbomer 940 was homogeneously dissolved in the ion exchange water. Pinon Negro 50% ethanol aqueous solution extract and polyoxyethylene (50-mole) oleyl alcohol ether were dissolved in 95% ethanol and this mixture was added to the water phase. Other ingredients were then added, and the mixture was neutralized and thickened with caustic soda and L-arginine.

EXAMPLE 27

Essence Formula

| | |
|---|---|
| A Phase | |
| Ethyl alcohol (95%) | 10.0 wt % |
| Polyoxyethylene (20-mole) octyl dodecanol | 1.0 |
| Pantothenyl ethyl ether | 0.1 |
| Pinon Negro methanol extract | 1.5 |
| Methyl paraben | 0.15 |
| B Phase | |
| Potassium hydroxide | 0.1 |
| C Phase | |
| Glycerine | 5.0 |
| Dipropylene glycol | 10.0 |
| Sodium hydrogen sulfite | 0.03 |
| Carboxyvinyl polymer (Product name: Carbomer 940 from B.F. Goodrich Chemical company) | 0.2 |
| Purified water | Balance |

Preparation Method

The A phase and the C phase were independently dissolved homogeneously, and then the A phase was added to the C phase and solubilized. The B phase was then added, and finally containers were filled.

EXAMPLE 28

Facial Pack Formula

| | |
|---|---|
| A Phase | |
| Dipropylene glycol | 5.0 wt % |
| Polyoxyethylene (60-mole) hardened castor oil | 5.0 |
| B Phase | |
| Pinon Negro methanol extract | 0.01 |
| Olive oil | 5.0 |
| Tocopherol acetate | 0.2 |
| Ethyl paraben | 0.2 |
| Perfume | 0.2 |
| C Phase | |
| Sodium hydrogen sulfite | 0.03 |
| Polyvinyl alcohol (Degree of saponification 90, degree of polymerization 2,000) | 13.0 |
| Ethanol | 7.0 |
| Purified water | Balance |

Preparation Method

The A, B and C phases were independently dissolved homogeneously, and then the B phase was added to the A phase and solubilized. The C phase was then added to this, and finally containers were filled.

EXAMPLE 29

Solid foundation Formula

| | |
|---|---|
| Talc | 43.1 wt % |
| Kaolin | 15.0 |
| Sericite | 10.0 |
| Zinc flower | 7.0 |
| Titanium dioxide | 3.8 |
| Yellow iron oxide | 2.9 |
| Black iron oxide | 0.2 |
| Squalene | 8.0 |
| Isostearic acid | 4.0 |
| POE sorbitan monooleate | 3.0 |
| Isocetyl octate | 2.0 |
| Pinon Negro ethanol extract | 1.0 |
| Preservative | Appropriate amount |
| Perfume | Appropriate amount |

Preparation Method

The powder ingredients, i.e. from talc to black iron oxide, were thoroughly mixed by a blender, and the oil-based ingredients, i.e. from squalene to isocetyl octate, Pinon Negro ethanol extract, the preservative and the perfume were added to this. After a thorough kneading, the product was filled into a container and molded.

EXAMPLE 30

Emulsified Foundation (cream type) Formula

| Powder Portion | |
|---|---|
| Titanium dioxide | 10.3 wt % |
| Sericite | 5.4 |
| Kaolin | 3.0 |
| Yellow iron oxide | 0.8 |
| Red iron oxide | 0.3 |
| Black iron oxide | 0.2 |
| Oil Phase | |
| Decamethylpentasiloxane | 11.5 |
| Liquid paraffin | 4.5 |
| Polyoxyethylene modified dimethylpolysiloxane | 4.0 |
| Water Phase | |
| Purified water | 50.0 |
| 1,3-butylene glycol | 4.5 |
| Pinon Negro ethanol extract | 1.5 |
| Sorbitan sesquioleic ester | 3.0 |
| Preservative | Appropriate amount |
| Perfume | Appropriate amount |

Preparation Method

After heating and stirring the water phase, the powder portion, thoroughly mixed and crushed, was added to it and the mixture was treated with a homo-mixer. The heat-mixed oil phase was then added to this mixture and the resulting mixture was treated with a homo-mixer. Finally, the perfume was added while the mixture was stirred and the temperature was lowered to room temperature.

Pinon Blanco Extract

1. Sample Preparation 50 g of stem and branch parts of Pinon Blanco were immersed in ethanol at room temperature for a week. The extract solution was then concentrated to obtain an ethanol extract. This extract was dissolved in DMSO to obtain a 1% solution, and this solution was diluted to adjust the concentration for the following experiments.

2. Cell Culture

B16 melanoma culture cells from mice were used. A culture was conducted in a CO2 incubator (95% air and 5% carbon oxide) at 37° C. using Eagle's medium containing 10% FBS and theophylline (0.09 mg/ml). After 24 hours of culturing, the sample solution was added to it such that the final concentration (in dried extract) was $10^{-2}$ to $10^{-5}$ wt %. The culture was continued for 3 more days, and melanine production was visually evaluated and the tyrosinase activity inihibition effect was measured.

3. Visual Evaluation of the Amount of Melanin

A diffusion plate was placed on top of the lid of the well plate, and the amount of melanin in the cells was evaluated using an inverted microscope. The evaluation was compared with that of a sample with no added Pinon Blanco extract (control sample). The results are shown in Table 7.

For a reference, the same testing was conducted on Nepeta japonica Maxim. (Lamium album L. subfamily, perilla family) extract which was already known to suppress melanin production. These results are also shown in Table 7. In the table, "toxicity" means there is cell toxicity.

Criteria:

○: White (amount of melanin)

Δ: Somewhat white (amount of melanin)

X: Control (amount of melanin)

4. Tyrosinase Activity Measurement

Before the measurement, the medium was removed, followed by washing twice with 100 microliters of PBS. 45 microliters of PBS containing 1% Triton X (surfactant from Rohm & Haas) was then added to each well. The plate was vibrated for 1 minute to thoroughly destroy the cell membranes, and the absorbance at 475 nm was measured using a microplate reader, which was defined as the absorbance at time 0 minutes. Quickly after this, 5 microliters of 10 mML-Dopa solution was added and the plate was transferred to an incubator kept at 37° C. to react for 60 minutes. The plate was vibrated for 1 minute and the absorbance (475 nm) at time 60 minutes was measured. The tyrosinase activity inhibition ratio (%) was defined as a decrease in the absorbance difference between time 0 minutes and time 60 minutes for the sample to which Pinon Blanco extract was added compared with the absorbance difference between time 0 minutes and time 60 minutes for the sample to which Pinon Blanco extract was not added. The results are shown in Table 7.

For a reference, the same testing was conducted on Nepeta japonica Maxim. extract which was already known to inhibit tyrosinase activity. These results are also shown in Table 7. In the table, "toxicity" means there is cell toxicity, and "-" indicates that no significant difference compared with the control was observed within 5%-level of significance.

TABLE 7

| Concentration (wt %) | Visual Evaluation of Melanin Production | | | | Tyrosinase Activity Activity Inhibition Ratio (%) | | | |
|---|---|---|---|---|---|---|---|---|
| | $10^{-5}$ | $10^{-4}$ | $10^{-3}$ | $10^{-2}$ | $10^{-5}$ | $10^{-4}$ | $10^{-3}$ | $10^{-2}$ |
| Pinon Blanco extract | X | ○ | ○ | ○ | 19 | 28 | 59 | 78 |
| Nepeta | X | X | X | X | — | — | — | 55 |

TABLE 7-continued

| Concen-tration (wt %) | Visual Evaluation of Melanin Production | | | | Tyrosinase Activity Activity Inhibition Ratio (%) | | | |
|---|---|---|---|---|---|---|---|---|
| | $10^{-5}$ | $10^{-4}$ | $10^{-3}$ | $10^{-2}$ | $10^{-5}$ | $10^{-4}$ | $10^{-3}$ | $10^{-2}$ |
| japonica Maxim. extract | | | | | | | | |

5. Whitening Effect Testing

Test Method 40 testees were exposed to summer sunlight for 4 hours (2 hours a day for 2 days) and the skin of an inner lateral part of their upper arm was used as the subject of the test. Beginning after 5 days from the day they were exposed to the sunlight, each sample was applied to this skin once in the morning and once in the afternoon for 4 weeks. The panel was divided into 5 groups 5 with 8 persons in each group. Testing was conducted using the following formulations.

| Alcohol Phase | |
|---|---|
| 95% ethyl alcohol | 55.0 wt % |
| Polyoxyethylene (25-mole) hardened castor oil ether | 2.0 |
| Antioxidant/preservative | Appropriate amount |
| Perfume | Appropriate amount |
| Drug (specified in Table 8) | |
| Water Phase | |
| Glycerine | 5.0 |
| Sodium hexamethaphosphate | Appropriate amount |
| Ion exchange water | Balance |

Preparation Method

The water phase and the alcohol phase were prepared separately and then mixed and solubilized.

Evaluation Method

The hypochromic effect after the application was evaluated based on the criteria below.

Criteria:

⊚: Very effective or effective on 80% or more of the testees

○: Very effective or effective on 50% to less than 80% of the testees

Δ: Very effective or effective on 30% to less than 50% testees

X: Very effective or effective on less than 30% of the testees

Samples were prepared with the blend compositions described in the aforementioned test Method, and the drugs listed in Table 8 were used to compare the whitening effect. The results are shown in Table 8.

TABLE 8

| Drug | Blend Ratio (5) | Effect |
|---|---|---|
| Nothing Added | – | X |
| Hydroquinone | 1.0 | Δ |
| Pinon Blanco extract | 0.1 | ○ |
| Pinon Blanco extract | 1.0 | ○ |
| Pinon Blanco extract | 10.0 | ⊚ |

The Pinon Blanco extracts in Table 8 were obtained by heated reduction of the whole plant of Pinon Blanco in ethanol, followed by filtering and concentration/drying.

As clearly shown in Table 8, it was confirmed that the samples with Pinon Blanco extract more effectively prevented excessive deposition of the melanin pigment and thus prevented darkening of the skin.

EXAMPLE 31

Cream Formula

| | |
|---|---|
| Stearic acid | 5.0 wt % |
| Stearyl alcohol | 4.0 |
| Isopropyl myristate | 18.0 |
| Glycerine monostearic ester | 3.0 |
| Propylene glycol | 10.0 |
| Pinon Blanco methanol extract | 0.01 |
| Caustic potash | 0.2 |
| Sodium hydrogen sulfite | 0.01 |
| Preservative | Appropriate amount |
| Perfume | Appropriate amount |
| Ion exchange water | Balance |

Preparation Method

Propylene glycol, the Pinon Blanco extract and caustic potash were added to the ion exchange water and the mixture was heated to and kept at 70° C. (water phase). Other ingredients were mixed, then heat-melted and the temperature was kept at 70° C. (oil phase). The oil phase was gradually added to the water phase, and after all of it had been added, the temperature was kept at that temperature to allow the mixture to react. Finally, the mixture was homogeneously emulsified by a homo-mixer and cooled to 30° C. while being thoroughly stirred.

EXAMPLE 32

Cream Formula

| | |
|---|---|
| Stearic acid | 2.0 wt % |
| Stearyl alcohol | 7.0 |
| Hydrated lanolin | 2.0 |
| Squalene | 5.0 |
| 2-octyldodecyl alcohol | 6.0 |
| Polyoxyethylene (25-mole) cetyl alcohol ether | 3.0 |
| Glycerine monostearic ester | 2.0 |
| Propylene glycol | 5.0 |
| Pinon Blanco extract | 0.05 |
| Sodium hydrogen sulfite | 0.03 |
| Ethyl paraben | 0.3 |
| Perfume | Appropriate amount |
| Ion exchange water | Balance |

Preparation Method

Propylene glycol was added to the ion exchange water and the mixture was heated to and kept at 70° C. (water phase). Other ingredients were mixed, then heat-melted and the temperature was kept at 70° C. (oil phase). The oil phase was added to the water phase, and after pre-emulsification, the mixture was homogeneously emulsified by a homo-mixer and cooled to 30° C. while being thoroughly stirred.

EXAMPLE 33

Cream Formula

| | |
|---|---|
| Solid paraffin | 5.0 wt % |
| Bees wax | 10.0 |
| Vaseline | 15.0 |

| | |
|---|---|
| Liquid paraffin | 41.0 |
| Glycerine monostearic ester | 2.0 |
| Polyoxyethylene (20-mole) sorbitan monolauric ester | 2.0 |
| Soap powder | 0.1 |
| Borax | 0.2 |
| Pinon Blanco acetone extract | 0.05 |
| Pinon Blanco ethanol extract | 0.05 |
| Sodium hydrogen sulfite | 0.03 |
| Ethyl paraben | 0.3 |
| Perfume | Appropriate amount |
| Ion exchange water | Balance |

Preparation Method

Soap powder and borax were added to the ion exchange water and the mixture was heated to and kept at 70° C. (water phase). Other ingredients were mixed, then heat-melted and the temperature was kept at 70° C. (oil phase). The oil phase was gradually added to the water phase while stirring was conducted to allow the reaction to occur. When the reaction was complete, the mixture was homogeneously emulsified by a homo-mixer and then cooled to 30° C. while being thoroughly stirred.

EXAMPLE 34

Emulsion Formula

| | |
|---|---|
| Stearic acid | 2.5 wt % |
| Cetyl alcohol | 1.5 |
| Vaseline | 5.0 |
| Liquid paraffin | 10.0 |
| Polyoxyethylene (10-mole) monooleic ester | 2.0 |
| Polyethylene glycol 1500 | 3.0 |
| Triethanol amine | 1.0 |
| Carboxyvinyl polymer (Product name: Carbomer 941 from B.F. Goodrich Chemical company) | 0.05 |
| Pinon Blanco ethyl acetate extract | 0.01 |
| Sodium hydrogen sulfite | 0.01 |
| Ethyl paraben | 0.3 |
| Perfume | Appropriate amount |
| Ion exchange water | Balance |

Preparation Method

Carboxyvinyl polymer was dissolved in a small amount of the ion exchange water (A phase). Polyethylene glycol 1500 and triethanol amine were added to and heat-dissolved in the rest of the ion exchange water, and the temperature was kept at 70° C. (water phase). Other ingredients were mixed, then heat-melted and the temperature was kept at 70° C. (oil phase). The oil phase was added to the water phase, and, after pre-emulsification, the A phase was added and the mixture was homogeneously emulsified by a homo-mixer and cooled to 30° C. while being thoroughly stirred.

EXAMPLE 35

Emulsion Formula

| | |
|---|---|
| Microcrystalline wax | 1.0 wt % |
| Bees wax | 2.0 |
| Lanolin | 20.0 |
| Liquid paraffin | 10.0 |
| Squalene | 5.0 |
| Sorbitan sesquioleic ester | 4.0 |
| Polyoxyethylene (20-mole) sorbitan monooleic ester | 1.0 |
| Propylene glycol | 7.0 |
| Pinon Blanco acetone extract | 10.0 |
| Sodium hydrogen sulfite | 0.03 |
| Ethyl paraben | 0.3 |
| Perfume | Appropriate amount |
| Ion exchange water | Balance |

Preparation Method

Propylene glycol was added to the ion exchange water and the mixture was heated to and kept at 70° C. (water phase). Other ingredients were mixed, then heat-melted and the temperature was kept at 70° C. (oil phase). The oil phase was gradually added to the water phase while stirring was conducted, and the mixture was homogeneously emulsified by a homo-mixer and then cooled to 30° C. while being thoroughly stirred.

EXAMPLE 36

Jelly Formula

| | |
|---|---|
| 95% ethyl alcohol | 10.0 wt % |
| Dipropylene glycol | 15.0 |
| Polyoxyethylene (50-mole) oleyl alcohol ether | 2.0 |
| Carboxyvinyl polymer (Product name: Carbomer 940 from B.F. Goodrich Chemical company) | 1.0 |
| Caustic soda | 0.15 |
| L-arginine | 0.1 |
| Pinon Blanco 50% ethanol aqueous solution extract | 7.0 |
| Sodium 2-hydroxy-4-methoxybenzophenone-sulfonate | 0.05 |
| Ethylenediamine-tetraacetic acid trisodium dihydrate | 0.05 |
| Methyl paraben | 0.2 |
| Perfume | Appropriate amount |
| Ion exchange water | Balance |

Preparation Method

Carbomer 940 was homogeneously dissolved in the ion exchange water. Pinon Blanco 50% ethanol aqueous solution extract and polyoxyethylene (50-mole) oleyl alcohol ether were dissolved in 95% ethanol and this mixture was added to the water phase. Other ingredients were then added, and the mixture was neutralized and thickened with caustic soda and L-arginine.

EXAMPLE 37

Essence Formula

| A Phase | |
|---|---|
| Ethyl alcohol (95%) | 10.0 wt % |
| Polyoxyethylene (20-mole) octyl dodecanol | 1.0 |
| Pantothenyl ethyl ether | 0.1 |
| Pinon Blanco methanol extract | 1.5 |
| Methyl paraben | 0.15 |
| B Phase | |
| Potassium hydroxide | 0.1 |
| C Phase | |
| Glycerine | 5.0 |
| Dipropylene glycol | 10.0 |
| Sodium hydrogen sulfite | 0.03 |
| Carboxyvinyl polymer (Product name: Carbomer 940 from B.F. Goodrich Chemical company) | 0.2 |
| Purified water | Balance |

Preparation Method

The A phase and the C phase were independently dissolved homogeneously, and then the A phase was added to the C phase and solubilized. The B phase was then added, and finally containers were filled.

EXAMPLE 38

Facial pack Formula

| A Phase | |
|---|---|
| Dipropylene glycol | 5.0 wt % |
| Polyoxyethylene (60-mole) hardened castor oil | 5.0 |
| B Phase | |
| Pinon Blanco methanol extract | 0.01 |
| Olive oil | 5.0 |
| Tocopherol acetate | 0.2 |
| Ethyl paraben | 0.2 |
| Perfume | 0.2 |
| C Phase | |
| Sodium hydrogen sulfite | 0.03 |
| Polyvinyl alcohol (Degree of saponification 90, degree of polymerization 2,000) | 13.0 |
| Ethanol | 7.0 |
| Purified water | Balance |

Preparation Method

The A, B and C phases were independently dissolved homogeneously, and then the B phase was added to the A phase and solubilized. The C phase was then added to this, and finally containers were filled.

EXAMPLE 39

Solid Foundation

| Talc | 43.1 wt % |
|---|---|
| Kaolin | 15.0 |
| Sericite | 10.0 |
| Zinc flower | 7.0 |
| Titanium dioxide | 3.8 |
| Yellow iron oxide | 2.9 |
| Black iron oxide | 0.2 |
| Squalene | 8.0 |
| Isostearic acid | 4.0 |
| POE sorbitan monooleate | 3.0 |
| Isocetyl octate | 2.0 |
| Pinon Blanco ethanol extract | 1.0 |
| Preservative | Appropriate amount |
| Perfume | Appropriate amount |

Preparation Method

The powder ingredients, i.e. from talc to black iron oxide, were thoroughly mixed by a blender, and the oil-based ingredients, i.e. from squalene to isocetyl octate, Pinon Blanco ethanol extract, the preservative and the perfume were added to this. After a thorough kneading, the product was filled into a container and molded.

EXAMPLE 40

Emulsified Foundation (cream type) Formula

| Powder Portion | |
|---|---|
| Titanium dioxide | 10.3 wt % |
| Sericite | 5.4 |
| Kaolin | 3.0 |
| Yellow iron oxide | 0.8 |
| Red iron oxide | 0.3 |
| Black iron oxide | 0.2 |
| Oil Phase | |
| Decamethylpentasiloxane | 11.5 |
| Liquid paraffin | 4.5 |
| Polyoxyethylene modified dimethyl-polysiloxane | 4.0 |
| Water Phase | |
| Purified water | 50.0 |
| 1,3-butylene glycol | 4.5 |
| Pinon Blanco ethanol extract | 1.5 |
| Sorbitan sesquioleic ester | 3.0 |
| Preservative | Appropriate amount |
| Perfume | Appropriate amount |

Preparation Method

After heating and stirring the water phase, the powder portion, thoroughly mixed and crushed, was added to it and the mixture was treated with a homo-mixer. The heat-mixed oil phase was then added to this mixture and the resulting mixture was treated with a homo-mixer. Finally, the perfume was added while the mixture was stirred and the temperature was lowered to room temperature.

As described above, the endermic liniment of the present invention has a melanin production suppression action and a tyrosinase activity suppression action and therefore exhibits superior hypochromic effects and whitening effects on pigment deposition, chloasma, freckles, liver spots, etc. after sunburn. This endermic liniment is also superior in terms of safety.

What is claimed is:

1. An endermic liniment in the form of an ointment, cream, emulsion, lotion, facial pack or bath additive comprising, on a dry basis, 0.005 to 20 wt % of a member selected from the group consisting of Cola de caballo extract, Piri-Piri extract, Pinon Negro extract, Pinon Blanco extract, and mixtures thereof, of the total endermic liniment.

2. The endermic liniment of claim 1, wherein the Cola de caballo extract comprises, on a dry basis, from about 0.01 to 10.0 wt %, of the total endermic liniment.

3. The endermic liniment of claim 1, wherein the Piri-Piri extract comprises, on a dry basis, from about 0.01 to 10.0 wt %, of the total endermic liniment.

4. The endermic liniment of claim 1, wherein the Pinon Negro extract comprises, on a dry basis, from about 0.01 to 10.0 wt %, of the total endermic liniment.

5. The endermic liniment of claim 1, wherein the Pinon Blanco extract comprises, on a dry basis, from about 0.01 to 10.0 wt %, of the total endermic liniment.

6. A process for suppressing production of melanin in the skin, comprising: applying to the skin an endermic liniment in the form of an ointment, cream, emulsion, lotion, facial pack or bath additive comprising, on a dry basis, 0.005 to 20 wt % of a member selected from the group consisting of Cola de caballo extract, Piri-Piri extract, Pinon Negro extract, Pinon Blanco extract, and mixtures thereof, of the total endermic liniment.

7. The process of claim 6, wherein the Cola de caballo extract comprises, on a dry basis, from about 0.01 to 10.0 wt % of the total endermic liniment.

8. The process of claim 6, wherein the Piri-Piri extract comprises, on a dry basis, from about 0.01 to 10.0 wt % of the total endermic liniment.

9. The process of claim 6, wherein the Pinon Negro extract comprises, on a dry basis, from about 0.01 to 10.0 wt % of the total endermic liniment.

10. The process of claim 6, wherein the Pinon Blanco extract comprises, on a dry basis, from about 0.01 to 10.0 wt % of the total endermic liniment.

* * * * *